United States Patent
Almeida (10) Patent No.: US 6,595,986 B2
(45) Date of Patent: *Jul. 22, 2003

(54) MULTIPLE PULSE PHOTO-DERMATOLOGICAL DEVICE

(76) Inventor: Stephen Almeida, 813 S. Westshore Blvd., Tampa, FL (US) 33609

( * ) Notice: Subject to any disclaimer, the term of this patent is extended or adjusted under 35 U.S.C. 154(b) by 0 days.

This patent is subject to a terminal disclaimer.

(21) Appl. No.: 09/841,816

(22) Filed: Apr. 25, 2001

(65) Prior Publication Data

US 2001/0029364 A1 Oct. 11, 2001

Related U.S. Application Data

(63) Continuation-in-part of application No. 09/173,422, filed on Oct. 15, 1998, now Pat. No. 6,228,074.

(51) Int. Cl.[7] ............................................... A61B 18/18
(52) U.S. Cl. ................................ 606/9; 606/3; 606/10; 607/88; 607/91; 128/898
(58) Field of Search ............... 606/3, 9, 10; 607/88–91; 128/898

(56) References Cited

U.S. PATENT DOCUMENTS

| 4,388,924 A | | 6/1983 | Weissmann et al. ...... 128/303.1 |
| 5,000,752 A | | 3/1991 | Hoskin ........................... 606/9 |
| 5,226,907 A | | 7/1993 | Tankovich ................... 606/133 |
| 5,282,842 A | * | 2/1994 | Changaris .................... 607/88 |
| 5,425,728 A | | 6/1995 | Tankovich ..................... 606/9 |
| 5,425,754 A | * | 6/1995 | Braun et al. .................. 607/88 |
| 5,474,549 A | | 12/1995 | Ortiz et al. .................... 606/9 |
| 5,486,172 A | | 1/1996 | Chess .......................... 606/20 |
| 5,595,568 A | | 1/1997 | Anderson et al. ............... 660/9 |
| 5,620,478 A | * | 4/1997 | Eckhouse ..................... 607/88 |
| 5,628,744 A | | 5/1997 | Coleman et al. .............. 606/12 |
| 5,630,811 A | | 5/1997 | Miller ........................... 606/9 |
| 5,632,741 A | | 5/1997 | Zavislan et al. ................ 606/9 |
| 5,647,866 A | | 7/1997 | Zaias et al. ..................... 606/9 |
| 5,683,380 A | * | 11/1997 | Eckhouse et al. ............... 606/9 |
| 5,735,844 A | | 4/1998 | Anderson et al. ............... 606/9 |
| 5,752,948 A | | 5/1998 | Tankovich et al. ............. 606/9 |
| 5,752,949 A | | 5/1998 | Tankovich et al. ............. 606/9 |
| 5,766,214 A | | 6/1998 | Mehl, Sr. et al. ............... 606/9 |
| 5,849,029 A | | 12/1998 | Eckhouse et al. ........... 607/104 |
| 5,868,732 A | | 2/1999 | Waldman et al. ............... 606/9 |
| 5,885,274 A | * | 3/1999 | Fullmer et al. ................ 606/9 |
| 5,961,543 A | * | 10/1999 | Waldmann ................... 607/88 |
| 6,050,990 A | | 4/2000 | Tankovich et al. ............. 606/9 |
| 6,161,544 A | * | 12/2000 | DeVore et al. .............. 128/898 |
| 6,168,590 B1 | * | 1/2001 | Neev ............................. 606/9 |
| 6,228,074 B1 | * | 5/2001 | Almeida ........................ 606/9 |
| 6,447,537 B1 | * | 9/2002 | Hartman ...................... 607/94 |
| 6,517,532 B1 | * | 2/2003 | Altshuler et al. ............... 606/9 |

\* cited by examiner

Primary Examiner—Linda C. M. Dvorak
Assistant Examiner—Ahmed M Farah
(74) Attorney, Agent, or Firm—Brown Rudnick Berlack Israels LLP; John C. Serio (57) ABSTRACT

Method and apparatus to cause the cessation of hair growth on a specific area of the body and for the treatment of unwanted dermatological conditions. The area of treatment is exposed to a particular pattern and wavelength of light generated by multiple flashlamps, which allow simultaneous, overlap, or consecutive firing. Controlling the intensity of light, the output wavelength and the delay between pulses allow treatment to be adjusted to different skin conditions and hair types. Skin damage is virtually eliminated by the length and characteristic shape of the individual pulse of light.

16 Claims, 8 Drawing Sheets

MULTIPLE PULSE PHOTO-DERMATOLOGICAL DEVICE

CROSS REFERENCE TO RELATED APPLICATION

This patent application claims priority from and is a continuation-in-part of U.S. patent application Ser. No. 09/173,422 filed Oct. 15, 1998 now U.S. Pat. No. 6,228,074 which is incorporated herein by reference in its entirety.

BACKGROUND OF THE RELATED ART

This disclosure relates to a painless method and related devices for causing temporary and/or permanent cessation of hair growth using flashlamps. Unwanted hair is an extremely common problem which can be caused by many reasons. There are many products and methods for temporarily and permanently removing hair. The methods can be very temporary such as in waxing, shaving, plucking and depilatory creams. These methods, however temporary, are very popular due to cost, quickness and/or absence of pain involved in the procedure. Electrolysis has been proven to be extremely slow and painful but is popular because of the claimed permanency and economical cost. Laser methods such as those described in U.S. Pat. No. 5,226,907 which uses a light absorbing cream in contact with the hair to create heat and destroy the hair have been shown to be painful and mostly temporary. Other laser treatments such as those stated in U.S. Pat. No. 5,595,568 use laser generated optical pulses directed through a transparent contact device which are absorbed by melanin in the hair follicle which consequently heats the follicle and permanently removes it. This method is effective but can be very painful since the high temperature necessary to destroy the hair follicle also destroys some surrounding tissue and skin which can result in hyperpigmentation, blistering and possible scarring.

SUMMARY

The present disclosure provides a method in which the unwanted hair growth can be removed without damage to the skin. One embodiment of the present disclosure is a method to cause cessation of hair growth of multiple hair follicles from a selected area of the skin in an efficient and painless manner. According to the disclosure, the method of hair removal consists of delivering a specific pattern of non-laser generated multiple light wavelengths which pass through the skin and into the hair and its components. The absorption of these various wavelengths results in thermal and photochemical damage to the hair and its components during the hair's Anagen phase which causes the primary effect of cessation of hair growth. While some treated areas will regenerate some regrowth, additional treatments will alleviate this residual hair growth. The multiple wavelengths that are utilized in this treatment occur at different intensities throughout the wavelength spectrum of 610 nm to 100 nm to produce a pattern that achieves optimal depth penetration. The multiple wavelength spectrum is produced by four flashlamps consisting of a specific mixture of krypton and xenon gas encased by a cerium doped synthetically fused quartz envelope. The four flashlamps are connected to separate user intensity controlled power supplies which are specifically designed to produce an 18 ms pulse duration with a specific pulse discharge pattern to accommodate different size hair follicles. Electrical supply energies of 160–400 joules are input to the flashlamps per cm2 of output. Each flashlamp can be fired simultaneously with an overlap or with a time duration of up to 40 ms between each pulse. The four flashlamps form a pulse train of four individual pulses which results in a treatment shot. Each treatment shot is separated by approximately 3 second intervals to allow the user to move the delivery system to another area of the body for subsequent treatment. The pulse length and characteristic shape of each individual pulse is designed to distribute the energy over a period of time that virtually eliminates damage to the skin which can occur in prior methods. This method also allows adjustment to the intensity of the light source and delay between each individual pulse. The ability to adjust the intensity and delay of the light source allows the user to adjust the treatment shot to accommodate different skin and hair types. The flashlamps utilized in the present disclosure are housed in a copper/zinc head which is connected to a hollow internally reflective rectangular light guide by means of a 610 nm high pass filter. The rim of the light guide is pressed against the skin so as to form an optical seal. The non-collimated light, consisting of wavelengths greater than 610 nm, passes through the 610 nm high pass filter and reflects at infinite angles down the hollow light guide into the skin reaching the hair and its components.

In an alternative embodiment of the disclosure, modification to the output wavelength pattern of the apparatus, by the use of a different light filter, allows the apparatus to be effective in destroying small blood vessels and melanin based pigmented lesions. Additionally, the altered output wavelength and the resulting use of the apparatus in destroying pigmented lesions further allow the apparatus to be utilized in skin smoothing, wrinkle smoothing and the rejuvenation of skin due to an increase in collagen after treatment.

BRIEF DESCRIPTION OF THE DRAWINGS

The foregoing and other features and advantages of the present disclosure will be more fully understood from the following detailed description of illustrative embodiments, taken in conjunction with the accompanying drawings in which.

DETAILED DESCRIPTION OF EXEMPLARY EMBODIMENTS

The exemplary embodiments and examples of use and operations disclosed are discussed in terms of a multi-pulse photo medical device, and more particularly, in terms of the use of various wavelengths of light that can be used in the removal of unwanted dermatological conditions. It is contemplated that the present disclosure finds applications to a wide variety of dermatological conditions including the removal of unwanted hair and skin lesions that are caused by the overabundance of small blood vessels. The device also finds use in the rejuvenation of skin by smoothing the skin and removing wrinkles that are associated with natural aging.

The following discussion includes a description of the various wavelengths of light and the intensity and duration of use which allows for the selective destruction of unwanted components of the skin surface. Reference will be now be made in detail to the exemplary embodiments of the disclosure, which are illustrated herein.

Figure 1:
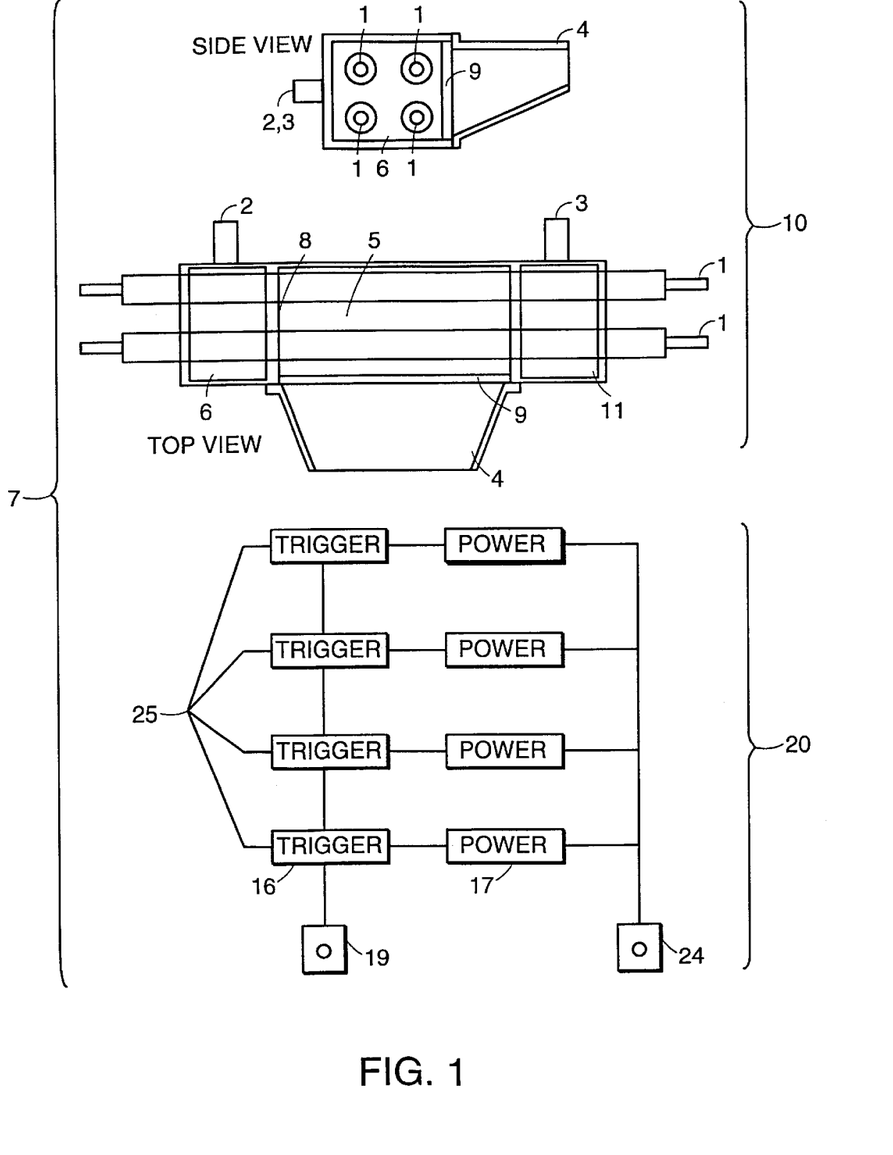
FIG. 1 is a cross sectional view of a delivery head of a device, in accordance with the principles of the present disclosure and a block diagram of the power supplies and controlling electronics which control the lamps in the delivery head.
Figure 4A:
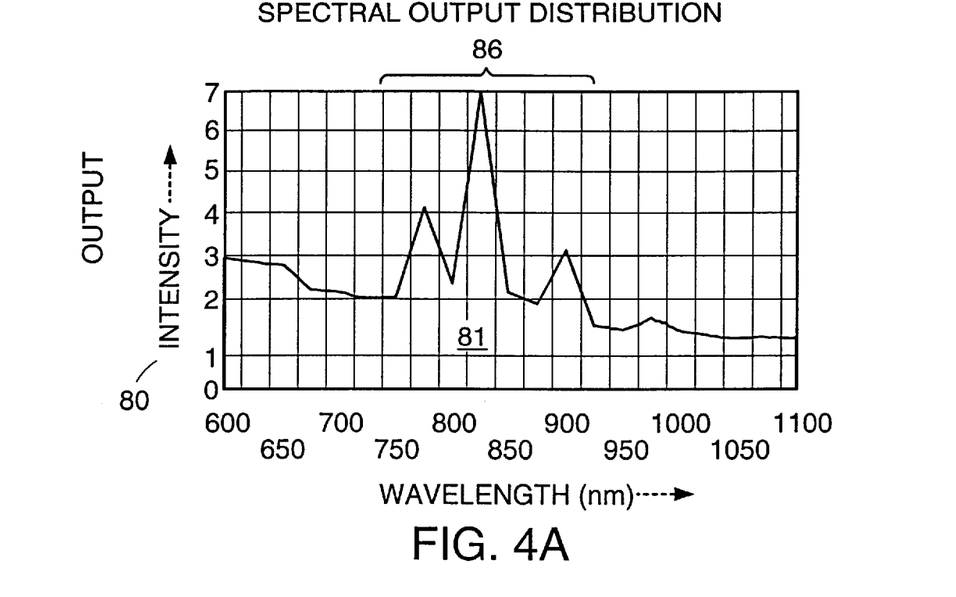
FIG. 4A is a graph showing a pattern of wavelengths generated.

Referring in detail to the drawings, a flashlamp apparatus generally identified by numeral 7, according to the present disclosure is shown in FIG. 1. Flashlamp apparatus 7 consists of a water-cooled delivery head 10 containing multiple flashlamps 1 each having an individual power source capable of timed firing 20 which causes cessation of the hair growth on the body. The multiple flashlamps 1 each contain a combination of approximately 90% krypton gas and 10% xenon gas. When charged, the combination of the krypton and xenon gases emit a specific pattern of wavelengths, which are shown in FIG. 4A. The container material of the flashlamps 1 is comprised of synthetic quartz to eliminate impurities. The use of synthetic quartz prevents the degradation of the flashlamps 1 after prolonged use. Additionally, the synthetic quartz is doped with cerium in order to block diffusion of ultraviolet light under 400 nm from the lamp and thereby maintaining the integrity of a reflective chamber 5 and a 610 nm high pass filter 9. The cerium doping also has the ability to convert ultraviolet light, which would normally become waste heat, into higher wavelengths which can pass through the high pass filter 9 to create a more efficient conversion of electrical energy to light output.

The reflective chamber 5 is made of a metallic material whose reflectivity coincides with the desired output of wavelengths greater than 610 nm. In one embodiment of the disclosure copper is used to construct the reflective chamber 5 as copper reflects over 95% of light at 620 nm and higher wavelengths while reflecting approximately 60% of light at lower wavelengths. Since the desired wavelength output is greater than 610 nm, this reflectivity of copper partially absorbs the lower wavelengths in the reflective chamber 5 so the high pass filter 9 does not bear the full absorption of the lower wavelengths which would result in damage to the high pass filter 9. Other reflective materials that are well known in the art can be used to construct the reflective chamber 5 these materials include but are not limited to gold, brass and ceramic. The delivery head 10 is cooled by water which flows in through an inlet port 2 and fills a first chamber 6, the water then flows over the flashlamps 1 into the reflective chamber 5 and then into a second chamber 11 and out an outlet port 3. The water, which flows through the delivery head 10, is recycled in a closed cooling system having a radiator and fan assembly, which uses room air as the heat exchange. The cooling system should maintain water temperatures surrounding the flashlamps 1 below a maximum continuous operating temperature of 100 degrees Celsius. Since the electrodes of flashlamps 1 create the greatest heat, chambers 6 and 11 allow a greater volume of water and thus thermal exchange over these areas. An optically transparent epoxy coating 8 is used to coat the metallic reflector to prevent oxidation and degradation from the water cooling which flows through the delivery head 10.

The commercially available high pass filter 9 transmits only wavelengths above 610 nm. Any lower wavelengths below 610 nm, that are produced, are absorbed and converted to heat. The cooling water in the reflective chamber 5 is also in contact with high pass filter 9 to extract heat due to the lower wavelength absorption. The high pass filter 9 only allows wavelengths above 610 nm to enter into a hollow reflective light guide 4. The hollow reflective lightguide 4 will be discussed in more detail in FIG. 2.

A power source and firing apparatus 20 are connected to the delivery head 10. The flashlamps 1 are connected to a control switch 25. Each flashlamp 1 is connected to its own power supply 17. Each power supply 17 supplies approximately 40 to 100 joules of electrical energy to each flashlamp 1 of every cm2 of output. A firing sequence control 19 is used to activate a trigger 16 for each flashlamp 1 in a simultaneous or consecutive order. An output intensity control 24 regulates the electrical energy of the individual power supplies 17, which discharge through the flashlamps 1. The firing sequence control 19 regulates the amount of time it takes for the output energy of one treatment shot to be dispersed while the output intensity control 24 regulates the amount of energy delivered.

Figure 2:
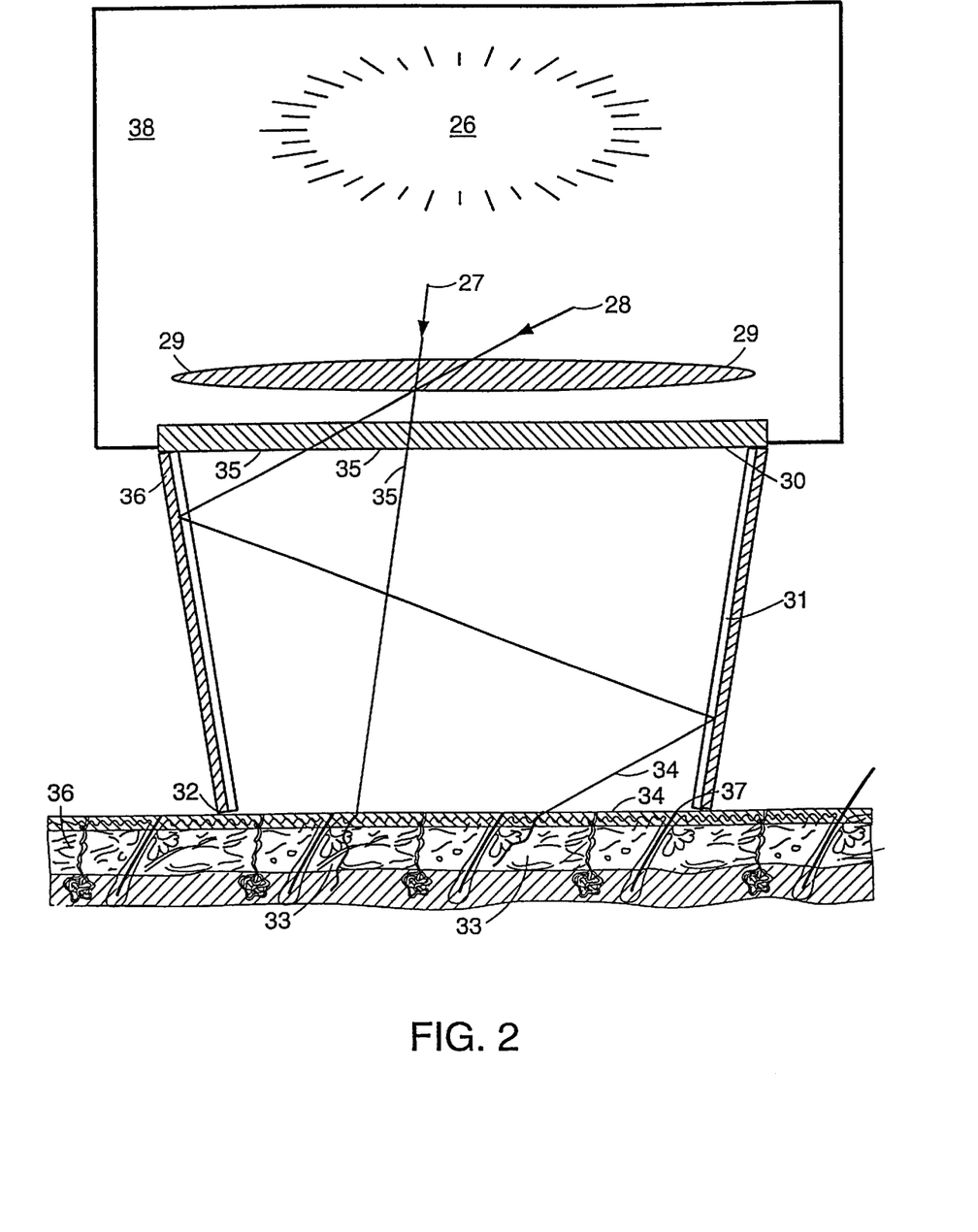
FIG. 2 is a cross sectional view of a hollow reflective light guide which guides photons to a target area of the skin.

Referring to FIG. 2, a cross sectional view of the hollow reflective light guide 4 is shown. The light source from the flashlamps 26 passes through the flashlamp cooling water 29 and is represented here by individual photons 27, 28. Since the light source 26 is non-laser, and radially emitted, the photons 27, 28 are reflected from the reflective chamber 38 and exit through the 610 nm high pass filter 30 (assuming the wavelength is higher than 610 nm), at multiple angles 35 down the reflective light guide 36 and into the skin at multiple angles 34 reaching the hair and its components 36 after scattering through the skin 33. The hollow reflective light guide 36, which is made of a metallic or ceramic highly reflective material for wavelengths above 610 nm, is coated with an optically transparent epoxy 31 to prevent oxidation and damage to the reflective material. The reflective light guide 36 is pressed against the skin 32 so as to form an optical seal so no light can escape outside the light guide. This optical seal ensures all energy is transmitted through the skin and into the hair and its components. The hair is trimmed or shaved prior to treatment so as to have no hair above the outer layer of skin that would absorb the light and block its transmission into the skin.

Figure 3A:
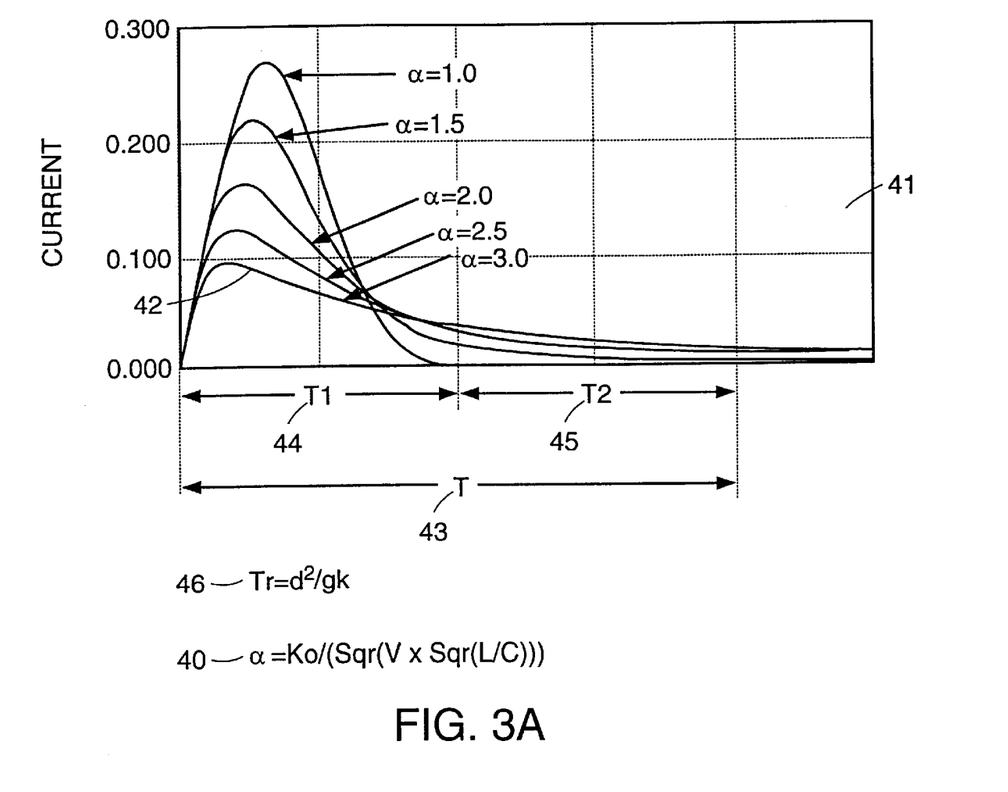
FIG. 3A is a graph showing a manipulated pulse geometry.

Turning now to FIG. 3A, a graphic representation of the pulse geometry and the pulse train sequence of one embodiment of the instant disclosure is shown. FIG. 3A shows the formula for damping factors 40 that create various pulse geometries shown in the graph 41. The desired pulse geometry that provides the most efficacious results for cessation of hair growth is damping factor of three (3), which provides an elongated pulse 42. This pulse geometry is desirable in that it takes advantage of the difference in thermal relaxation times of hair and skin. Thermal relaxation time is the time it takes for a body of particular size, shape, and material to dissipate 50% of its heat energy. The physical law is represented by equation 46 where d is the diameter of the body, g is the geometric factor, and k is the thermal diffusivity factor of the material. One reason for using this specific pulse geometry as depicted in FIG. 3a, is that it spreads the energy more evenly throughout the pulse length T 43 which is approximately 18 ms for the device. Since the thermal relaxation time of skin is approximately 10 ms, having the pulse duration over 10 ms prevents damage to the skin by allowing the skin to dissipate the energy and thus avoiding damaging high temperatures. An additional advantage of this pulse geometry is to take advantage of the thermal relaxation time of hair follicles. Since hair follicle sizes vary in any particular area of the body, so do their corresponding thermal relaxation times. The optimum pulse duration and geometry would be one that can be effective on the broad sizes of hair follicles while sparing damage to the surrounding tissue. The average size hair follicles vary in thermal relaxation times from 20 ms to 100 ms. By using this specific pulse geometry, optimum damage is confined to the hair follicle for large and small hair follicles. Small follicles having a thermal relaxation time of 20 ms would dissipate the heat into the surrounding tissue rapidly resulting in a lower peak temperature in the hair follicle and creating high temperatures in the tissue. By using this specific pulse geometry 42, greater then 70% of the energy is delivered in the first half of the pulse T1 44 while the remaining energy is dispersed in the second half of the pulse T2 45. This still allows adequate cooling time for the skin but now creates higher temperatures in the small hair follicles since most of the energy is delivered in a short amount of time not allowing the follicle time to disperse the energy to the surrounding tissue. Large hair follicles having higher thermal relaxation times up to 100 ms are also effected since even more time is required to disperse the energy.

Figure 3B:
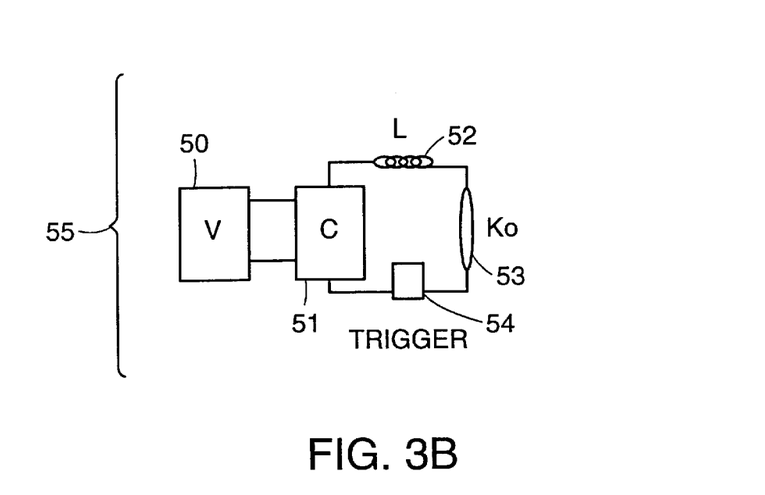
FIG. 3B is a schematic showing basic circuit components to adjust pulse geometry.

Referring to FIG. 3B, a schematic of the flashlamp circuit 55 necessary to accomplish this pulse geometry is shown. A voltage supply 50 charges a capacitor 51. When a trigger voltage 54 is applied to the flashlamp 53 it ionizes allowing the power from the capacitor 51 to pass through a inductor 52 and into the flashlamp 53 which has a certain resistance known as Ko. The values of the components in the circuit 55 must provide a damping factor of three (3) when inserted into formula 40 and also provide a pulse duration T, as shown in FIG. 3A, 43 of 18 ms.

Figure 3C:
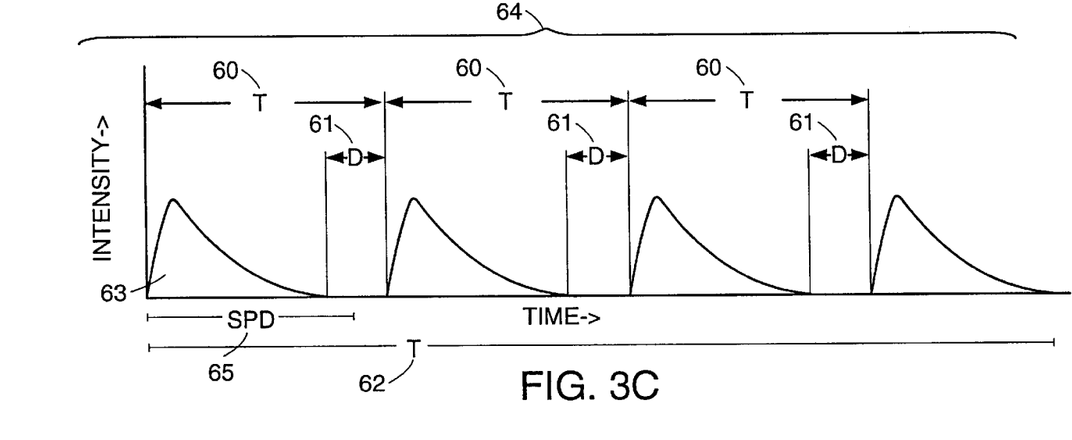
FIG. 3C is a graph showing the quad pulse train of each treatment shot and the controlled delay between each pulse.

Referring to FIG. 3C, a treatment shot from the apparatus, when the treatment shot is set for consecutive firing with delays between each pulse, is shown. The treatment shot consists of a four-pulse sequence train with a time delay between each pulse 64. A single pulse 63 is fired from the apparatus with a time delay of T 60 before the next consecutive pulse in the four-pulse train is triggered. If T 60 is greater than the single pulse duration (SPD) 65, which is approximately 18 ms, then a delay D 61 is created between each pulse. This delay 61 between each pulse allows the skin to cool before then next consecutive pulse is triggered. The total time it takes the apparatus to deliver the energy is T 62 which is the combination on all the delays 61 and all the SPDs 64. This time T 62 is the duration of the treatment shot. Each treatment shot is separated by approximately three-second interval to allow the user to move the delivery head to the next consecutive are for treatment.

Figure 3D:
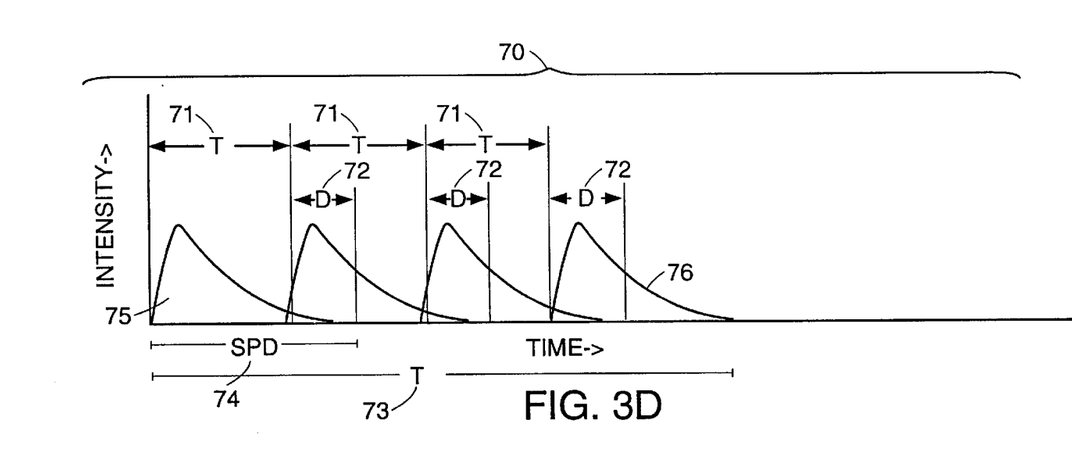
FIG. 3D is a graph showing the quad pulse train of each treatment shot with a negative delay that signifies overlap.

Referring to FIG. 3D, a treatment shot from the apparatus when the treatment shot is set for overlap firing is shown. The treatment shot consists of an overlap of single pulses in the four-pulse train 70. Since the flashlamps are connected to separate power supplies, the apparatus is capable of overlapping pulses. If a single pulse is fired from the apparatus 75 with a consecutive triggering time delay T 71 which is shorter than the SPD 74, then a negative delay (−) D 72 is created which represents an overlap of the consecutive pulses. This overlap transforms the four single pulses into a single sawtooth appearing pulse 76 of duration T 73. This single sawtooth pulse 76 allows more energy in a shorter amount of time T 73 than a single lamp system incapable of overlap. This higher energy in a shorter amount of time allows for more treatment options.

Figure 4B:
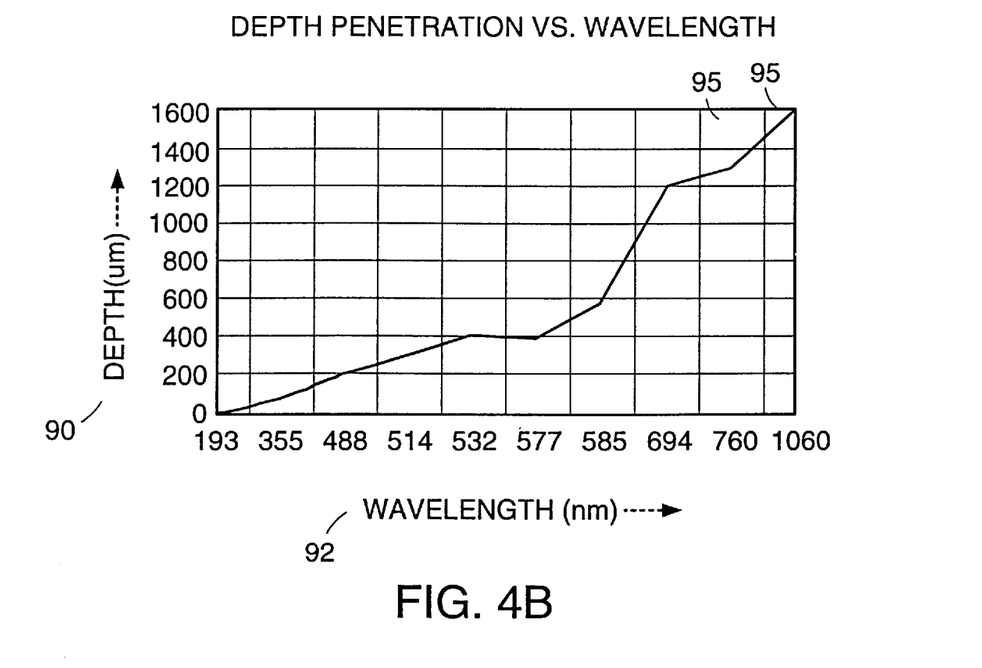
FIG. 4B is a graph representing the depth penetration of light with respect to wavelength.

Referring now to FIGS. 4A and 4B, the spectral output patterns and depth penetration of the light generated by the apparatus respectively, are shown. FIG. 4A refers to a graph of the output intensity 80 of the different wavelengths 81 generated by the apparatus. The majority of the light output is in the 725 nm to 925 nm wavelengths 86 as depicted on the graph as the three peaks.

Referring to FIG. 4B which graphically depicts the penetration depth 90 of light versus its wavelength 92. Since hair follicles and its components are located deep in the dermis, depth penetration of the incident light is very important. The output of the flashlamps, are designed to generate a large amount of deep penetrating wavelengths. The peak output wavelengths 95 of the flashlamps exhibit very good depth penetration allowing the incident light to reach the target hair and its components.

Figure 5A:
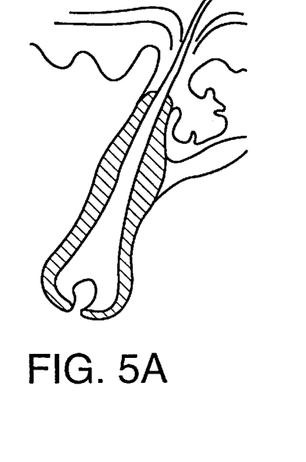
FIGS. 5A, 5B, 5C shows the cross sectional view of the different growth stages of a hair and its components.
Figure 5B:
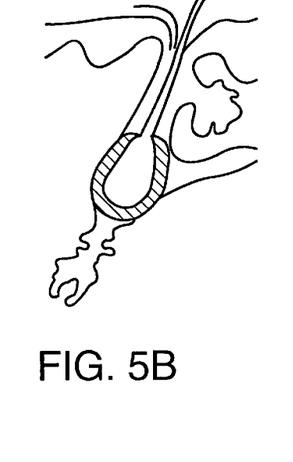
Figure 5C:
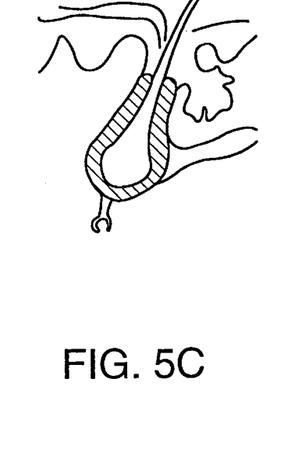

Referring to FIGS. 5A, 5B, 5C and 5D, which show the three stages of hair growth and its components. All hair goes through a three-stage cycle. FIG. 5A shows the growth stage (Anagen phase) of hair and its components. This Anagen phase is when the hair is actively growing. FIG. 5B is the transition phase (Catagen phase) when growth slows down. FIG. 5C shows the resting stage (Telogen phase) when the hair and its components are no longer active and growing. The apparatus of the present disclosure is most effective during the Anagen phase. It is believed that the absorption of light is greater at this time due to the enlargement of hair components. It has been found that the apparatus of the present disclosure has a greater effectiveness on hair during its Anagen phase and treatment during this phase will cause cessation of hair growth. It is contemplated that the apparatus is also effective during the other phases.

Figure 5D:
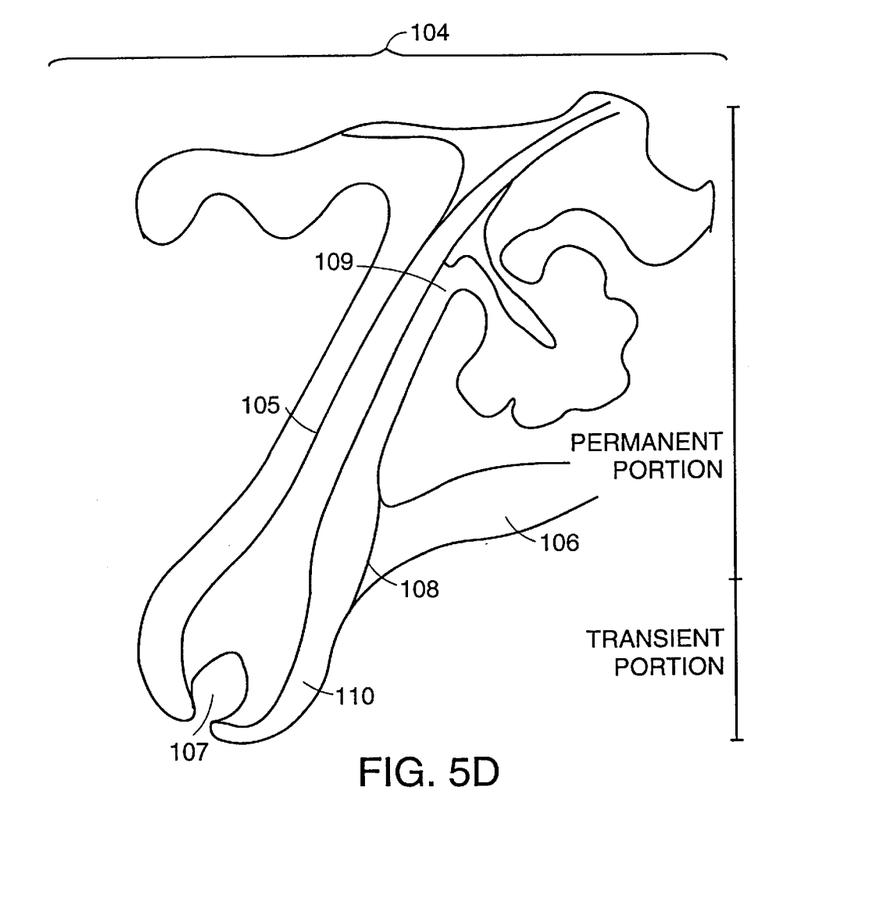
FIG. 5D shows a cross-sectional view of a hair and its components.

Referring to FIG. 5D which also shows hair and its components. The light output of the apparatus 104 is represented here by individual photons 105–110. These photons 105–110 penetrate through the skin and into the hair and its various components. The result of this photon absorption causes both thermal and photochemical damage to the hair and its components resulting in cessation of hair growth.

Figure 6A:
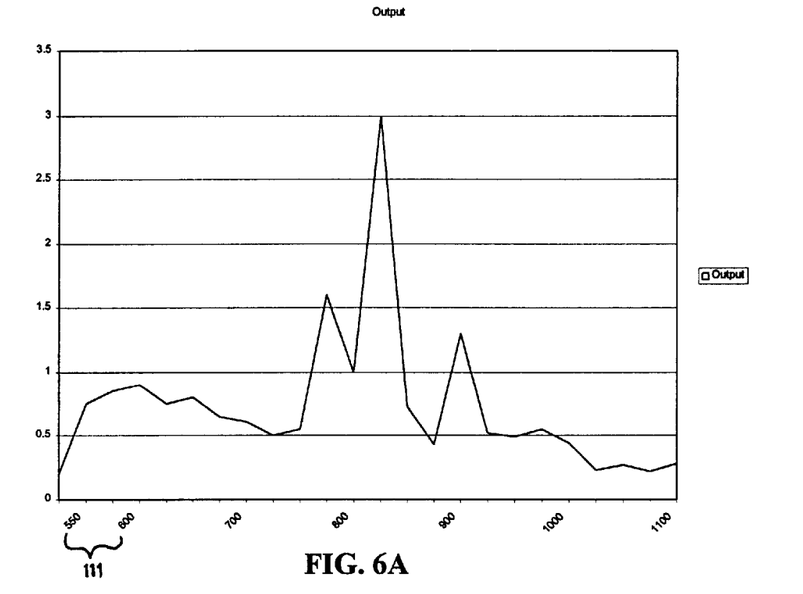
FIG. 6A is a graph showing a wavelength output between 530 nm to 610 nm.
Figure 6B:
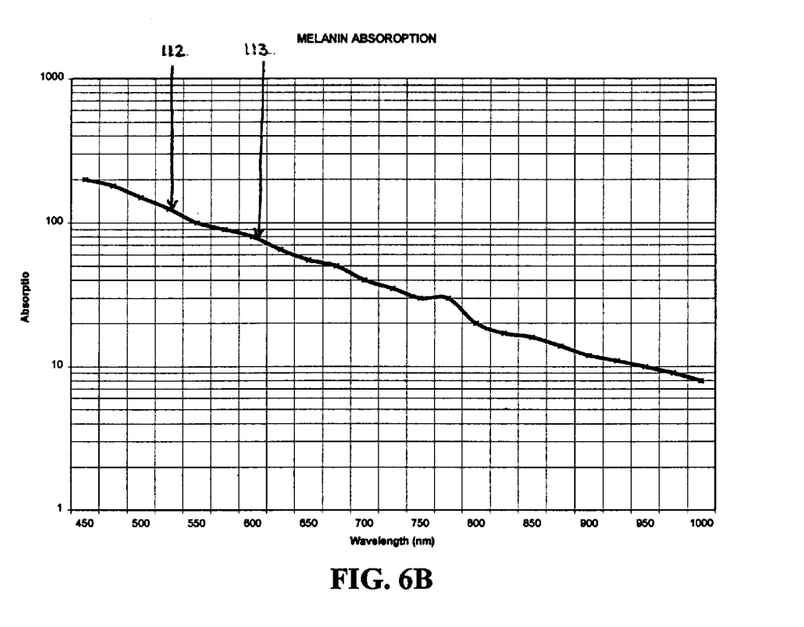
FIG. 6B is a graph showing the relationship of melanin adsorption in relationship to wavelength output.
Figure 6C:
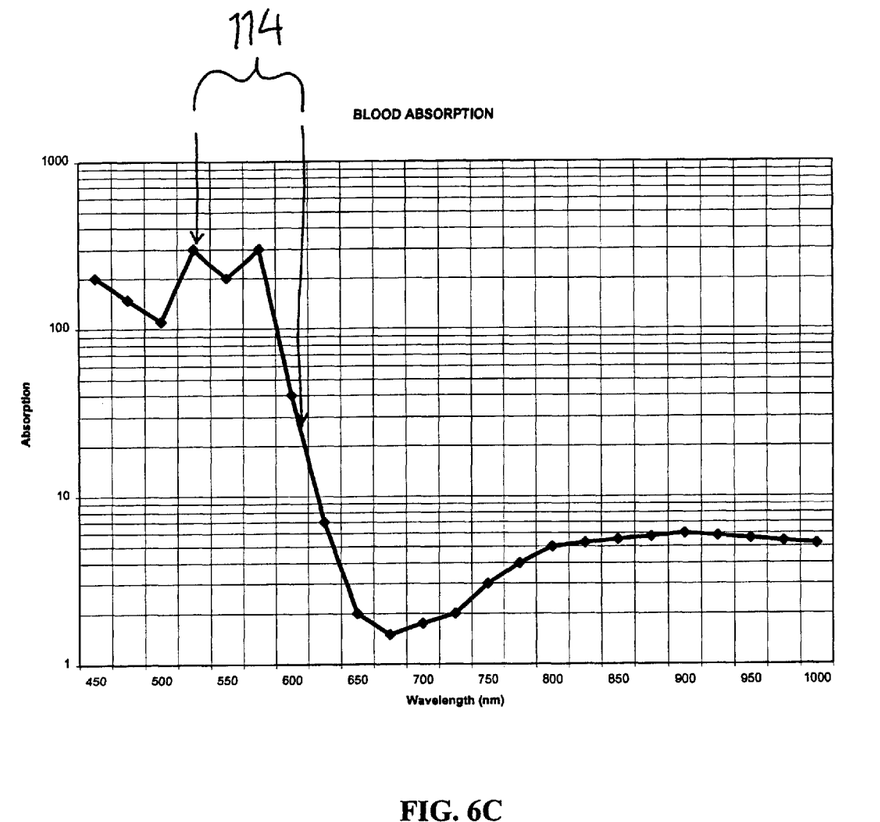
FIG. 6C is a graph showing the relationship between hemoglobin adsorption in relationship to wavelength output.

Referring to FIGS. 6A, 6B and 6C, an alternative embodiment of the present disclosure is shown. This alternative illustrative embodiment depicts how the apparatus can be easily modified to change the output wavelength pattern making the apparatus effective in destroying small blood vessels and melanin based pigmented lesions. By changing the value on the long pass filter as shown in FIG. 1, from 610 nm to 530 nm, an additional output of wavelengths 111 between 530 nm to 610 nm is created as shown in FIG. 6A. The difference in melanin absorption between the output wavelengths of 530 nm 112 and 610 nm 113 is approximately 60% increase as shown in FIG. 6B. This increase in melanin absorption allows for the alternative embodiment of the present disclosure to be useful in heating and destroying pigmented lesions. A further result of adjusting the output wavelengths in the alternative embodiment, in addition to destroying pigmented lesions, is a change in the appearance of the skin. The change in wavelength output facilitates the use of the alternative embodiment in skin smoothing, wrinkle smoothing, by causing a rejuvenating appearance of the skin. The additional wavelengths 111 shown in FIG. 6A, also allow the alternative embodiment to be effective in destroying small blood vessels. Hemoglobin absorption throughout the wavelength spectrum is shown in FIG. 6C. The additional wavelength output between 530 nm and 610 nm exhibits very high hemoglobin absorption 114 as seen in FIG. 6C. This high hemoglobin absorption allows the apparatus to heat and destroy small blood vessels Although the apparatus described in the illustrative embodiment herein contains four flashlamps, it should be appreciated by those skilled in the art that the delivery head of the apparatus may contain more or less than four flashlamps depending on the application and the area of treatment. Similarly, the pulse train may consist of more or less than four pulses depending on the characteristic and severity of various dermatological conditions that are to be treated. In addition, the ratio and amount of krypton and xenon in the flashlamps may be altered to produce a slightly different wavelength output pattern or various light filters that are well known in the art may be used to eliminate unwanted wavelengths.

The foregoing has been a description of illustrative embodiments of the present disclosure. The present disclosure is not to be limited in scope by the illustrative embodiments described which are intended as specific illustrations of individual aspects of the disclosure, and functionally equivalent methods and components are within the scope of the disclosure. Indeed, various modifications of the disclosure, in addition to those shown and described herein will become apparent to those skilled in the art from the foregoing description. Such modifications are intended to fall within the scope of the appended claims

What is claimed is:

1. A method of treatment for dermatological conditions comprising the steps of:
   (a) generating a light from multiple lamps having a specific wavelength output and intensity;
   (b) filtering said light through a high pass light filter to eliminate unwanted segments of said light;
   (c) placing a hollow reflective light guide against a skin section forming an optical seal to contain said light; and
   (d) illuminating said skin section by directing said light from multiple lamps through said filter through said hollow light guide.

2. The method of claim 1, wherein said light has a specific pulse geometry.

3. The method of claim 2, wherein said light source comprises multiple individual flashlamps that are fired simultaneously or consecutively with a delay between each said pulse.

4. The method of claim 3, wherein said pulses from said flashlamps are approximately 18 ms in duration.

5. The method of claim 3, wherein said flashlamps are individually powered by an electrical energy supply that is 160–400 joules for every cm2 of output.

6. The method of claim 1, wherein said light exiting said hollow light guide has a wavelength greater than 610 nm.

7. The method of claim 1, wherein said light exiting said hollow light guide has a wavelength greater than 530.

8. The method of claim 1, wherein said hollow reflective light guide is made of copper.

9. The method of claim 1 wherein said light spectral output pattern is generated in an output between 610 nm and 1,200 nm.

10. The method of claim 1 wherein said light spectral output patter is generated in an output between 530 nm and 1200 nm.

11. The method of claim 1, wherein said dermatological conditions are selected from the group consisting of unwanted hair growth, pigmented lesions, skin smoothing and skin rejuvenation.

12. The method of claim 1, wherein said light source comprises:
   a power source;
   a plurality of flashlamps;
   a water cooling system;
   a control source for firing said flashlamps.

13. The method as described in claim 8 wherein said flashlamps consist of Kr,Xe gas.

14. The method of claim 12, wherein said control source allows simultaneous, overlap and consecutive firing of the said flashlamps.

15. The method of claim 12, wherein said flashlamps consist of synthetically fused quartz doped with cerium.

16. An apparatus for treating a dermatological condition comprising:
   a water cooled delivery head;
   a plurality of flashlamps contained within said delivery head wherein said flashlamps produce a desired light output;
   an individual energy source connected to said flashlamps;
   a control mechanism connected to said individual energy source wherein said control mechanism allows simultaneous, overlapping and consecutive firing of the said flashlamps;
   a light filter positioned beneath said delivery head wherein said light filter eliminates specific wavelengths of light; and
   a hollow reflective light guide directing said light to a treatment area.

* * * * *